US005276238A

United States Patent [19]

Doyle

[11] Patent Number: 5,276,238

[45] Date of Patent: Jan. 4, 1994

[54] CO-OLIGOMERIZATION PROCESS

[75] Inventor: Michael J. Doyle, Amsterdam, Netherlands

[73] Assignee: Shell Oil Company, Houston, Tex.

[21] Appl. No.: 894,666

[22] Filed: Jun. 5, 1992

[30] Foreign Application Priority Data

Jul. 29, 1991 [GB] United Kingdom ................ 9116297

[51] Int. Cl.[5] .......................... C07C 2/30; C07C 2/26

[52] U.S. Cl. .................................... 585/511; 585/510; 585/521; 585/523; 585/525

[58] Field of Search ................................ 585/510, 511

[56] References Cited

U.S. PATENT DOCUMENTS

| | | | |
|---|---|---|---|
| 3,709,853 | 1/1973 | Karapinka | 585/511 |
| 4,045,508 | 8/1977 | Cupples et al. | 585/511 |
| 4,062,883 | 12/1977 | Hawthorne et al. | 502/159 |
| 4,855,523 | 8/1989 | Stevens et al. | 585/511 |
| 5,077,255 | 12/1991 | Welborn, Jr. | 502/104 |
| 5,116,795 | 5/1992 | Fries | 585/512 |
| 5,147,949 | 9/1992 | Chang | 502/117 |
| 5,162,466 | 11/1992 | Karol et al. | 502/103 |
| 5,169,818 | 12/1992 | Antberg et al. | 502/103 |

FOREIGN PATENT DOCUMENTS

| | | |
|---|---|---|
| 277003 | 8/1988 | European Pat. Off. . |
| 0443686 | 8/1991 | European Pat. Off. . |
| 1353873 | 7/1972 | United Kingdom . |

OTHER PUBLICATIONS

Hlatky et al., "Ionic, Base-Free Zirconocene Catalysts for Ethylene Polymerization", J. Am. Chem. Soc., 1989, vol. 111, pp. 2728-2729.

Shelly et al., "n[1]-Benzene Coordination: The Synthesis and X-Ray Crystal Structure of a Novel Silver Salt of the Weakly Coordinating Carborane Anion $B_{11}CH_{12}$," J. Am. Chem. Soc., 1985, vol. 107, pp. 5955-5959.

*Primary Examiner*—Anthony McFarlane

[57] ABSTRACT

A process for the preparation of olefins of the general formula $(CH_2—CH_2)_p—CH{=}CH_2$ in which formula R is a hydrocarbyl group and p is an integer of at least 1, comprising reacting ethene with at least one additional alpha olefin of the general formula $R—CH{=}CH_2$ under oligomerization conditions in the presence of a catalyst system comprising a first component which is a bis(cyclopentadienyl) Group IVA metal compound containing a substituent which is attached to the metal and which is capable of reacting with a cation, and a second component which is a compound having a bulky anion containing a plurality of boron atoms and which is substantially non-coordinating under the reaction conditions and a cation, and recovering an oligomeric product comprising linear olefins of the general formula $R—(CH_2—CH_2)_p—CH{=}CH_2$, wherein the additional alpha olefin(s) and ethene are present in a molar ratio of at least 1 and wherein at least one of the cyclopentadienyl groups of the metal compound is (cyclo)alkyl and/or arylalkyl substituted.

15 Claims, No Drawings

CO-OLIGOMERIZATION PROCESS

FIELD OF THE INVENTION

This invention relates to a co-oligomerization process and is particularly directed to the preparation of olefins of the general formula R—$(CH_2—CH_2)_p$—CH═$CH_2$ in which formula R is a hydrocarbyl group and p is an integer of at least 1, comprising reacting ethene with at least one further alpha olefin of the general formula R—CH═$CH_2$.

BACKGROUND OF THE INVENTION

Oligomerization processes for the production of linear alpha X olefins are well known. For example, from GB-A-1353873 it is known that $C_6$—$C_{20}$ linear alpha olefins can be prepared from ethene by oligomerization in the presence of a nickel containing catalyst. Linear olefins, especially linear alpha olefins, over a range of carbon chain lengths have found use as valuable intermediates in the preparation of polyolefins, detergents and lubricant additives. While the known processes for the oligomerization of ethene provide linear olefins of which the number of carbon atoms is even, for certain application areas of olefins, it is desirable to have olefins which have special structural features, such as linear alpha olefins which have an odd number of carbon atoms or alpha olefins which have one or more hydrocarbyl substituents located at or near the end of the carbon chain opposite to the end at which the double bond is located. The object of the present invention is the provision of an oligomerization process by which olefins having such special structural features can conveniently be prepared.

A process for the preparation of olefins of the general formula R—$(CH_2—CH_2)_p$—CH═$CH_2$ in which formula R is a hydrocarbyl group and p is an integer of at least 1, comprising reacting ethene with at least one further alpha olefin of the general formula R—CH═$CH_2$ under oligomerization conditions in the presence of a catalyst system obtainable by combining a first component which is a bis(cyclopentadienyl) Group IVA metal compound containing a substituent which is attached to the metal and which is capable of reacting with a cation, and a second component which is a compound having a bulky anion containing a plurality of boron atoms and which is substantially non-coordinating under the reaction conditions and a cation, and recovering an oligomeric product comprising linear olefins of the general formula R—$(CH_2—CH_2)_p$—CH═$CH_2$, is the subject matter of European Patent No. 91200367.0. By this co-oligomerization process it is possible to prepare mixtures comprising co-oligomers of high linearity which may have an odd or an even number of carbon atoms and which have a high content of alpha olefins. These oligomeric products are prepared in conjunction with oligomers of ethene from which they have to be separated in order to obtain them in a state of high purity. This separation may in some instances be difficult to perform.

It has now been found that, when in this process the further alpha olefin, designated by the general formula R—CH═$CH_2$, in which R is defined as hereinbefore, is present in the reaction mixture in a quantity of at least 1 mole per mole of ethene and at least one of the cyclopentadienyls of the metal compound is (cyclo)alkyl and/or arylalkyl substituted, an oligomerization product can be obtained which has a high content of olefins of the general formula R—$(CH_2—CH_2)_p$—CH═$CH_2$, in which R and p have the meanings given hereinbefore. The oligomerization product thus obtained has a very low content of other oligomers, for example oligomers of ethene and co-oligomers of ethene and the further alpha olefin, such as co-oligomers which have the double bond in the 2-position.

As products of the general formula R—$(CH_2—CH_2)_p$—CH═$CH_2$ may comprise linear alpha olefins which have an odd number of carbon atoms or alpha olefins which have one or more hydrocarbyl substituents located at or near the end of the carbon chain opposite to the double bond, the present process is capable of providing olefins with special structural features as indicated hereinbefore, in a single step from readily available feedstock. The desired oligomeric alpha-olefins can be prepared with relatively little formation of by-products and, accordingly, they can be purified relatively easily. The present process therefore constitutes an improvement over the process described in European Patent No. 91200367.0.

SUMMARY OF THE INVENTION

The present invention provides a process for the preparation of olefins of the general formula R—$(CH_2—CH_2)_p$—CH═$CH_2$ in which formula R is a hydrocarbyl group and p is an integer of at least 1, which process comprises reacting ethene with at least one additional alpha olefin of the general formula R—CH═CH under oligomerization conditions in the presence of a catalyst system comprising a first component which is a bis(cyclopentadienyl) Group IVA metal compound containing a substituent which is attached to the metal and which is capable of reacting with a cation, and a second component which is a compound having a bulky anion containing a plurality of boron atoms and which is substantially non-coordinating under the reaction conditions and a cation, and thereafter recovering an oligomeric product comprising linear olefins of the general formula R—$(CH_2—CH_2)_p$—CH═$CH_2$, wherein the additional alpha olefin(s) and ethene are present in a molar ratio of at least 1 and wherein at least one of the cyclopentadienyl groups of the metal compound is (cyclo)alkyl and/or arylalkyl substituted.

DESCRIPTION OF THE PREFERRED EMBODIMENTS

Metals of Group IVA are as defined in the Periodic Table of the Elements published in Kirk-Othmer, Encyclopaedia of Chemical Technology, 2nd edition, Vol. 8, p. 94.

The starting reactants comprise ethene, which may be supplied in the form of an ethene-containing gas together with an inert diluent such as nitrogen or helium. The further alpha olefins are suitably alpha olefins containing from 3 to about 20 carbon atoms, such as 1-butene, 4-methyl-1-pentene, 5,5-dimethyl-1-hexene, styrene or allylbenzene, dependent on the desired oligomerisation product. Mixtures of alpha olefins may also be employed.

When the further alpha olefin is linear and has an odd number of carbon atoms, the oligomeric products R—$(CH_21'CH_2)_p$—CH═$CH_2$ comprise olefins having odd numbers of carbon atoms. It appeared unexpectedly that when oligomeric branched olefins are formed as by-products, these branched olefins are to a large extent iso-alkenes of the general formula R—(C-

$H_2$—$CH_2)_p$—CR=$CH_2$, in which formula R and p have the meanings given hereinbefore, especially when the oligomerization is carried out at a temperature below about 120° C., in particular below about 100° C. As the additional olefin has an odd number of carbon atoms, these iso-alkenes have even numbers of carbon atoms. As a consequence, the desired linear oligomerisation products differ from the iso-alkenes by at least one carbon atom and can therefore relatively easily be recovered by separation from the iso-alkenes, for example by distillation. Thus, in the case that the additional alpha olefin is linear and has an odd number of carbon atoms it is an unexpected advantage of the present process that the linear oligomerization products can relatively easily be obtained in a purified state. Accordingly, the preferred further alpha olefin is linear and has an odd number of carbon atoms, in particular of less than 20, for example, propene, 1-pentene and 1-heptene or mixtures thereof. The most preferred further alpha olefin is propene.

The relative proportions of starting monomers present in the reaction mixture should be at least 1 mole of the further alpha olefin(s) per mole of ethene. Suitably the quantity of the alpha olefin(s) is at least about 20 moles per mole of ethene, more suitably at least about 50 moles per mole of ethene. Preferably the quantity of the alpha olefin(s) is less than about 1000 moles per mole of ethene, more preferably less than about 500 moles per mole of ethene. Ethene and the additional olefin(s) may be supplied at the initial stage of the co-oligomerization. In a preferred embodiment of the present process, the ethene to be reacted is only partly supplied at the initial stage of the reaction, the remainder of the ethene is supplied during the course of the reaction, typically at a rate which is suitable to replenish the ethene consumed.

To effect oligomerization, the reaction is suitably carried out at elevated temperatures, preferably in the range of from about 20° C. to about 175° C., more preferably from about 50° C. to about 150° C. The reaction is suitably carried out under conditions of moderate elevated pressure, preferably in the range of from 1 bar to about 100 bar, more preferably from about 5 to about 60 bar. The optimum conditions of temperature and pressure used for a particular catalyst system to maximize the yield of the desired oligomer and minimize competing reactions such polymerization can readily be determined by those skilled in the art.

The catalyst system, which may be formed initially prior to introduction to the reaction vessel, or which may be formed in situ, may be obtained by combining a first component which is a bis(cyclopentadienyl) Group IVA metal compound having a substituent which is attached to the metal and which is capable of reacting with a proton and with at least one of the cyclopentadienyl groups being (cyclo)alkyl and/or arylalkyl being substituted, and a second component which is an ionic combination of a bulky anion containing a plurality of boron atoms and a proton-donating cation, the anion being such that it is substantially non-coordinating under the reaction conditions employed. Thus, it is intended that the anion should not coordinate, or at least coordinate only weakly, to the bis(cyclopentadienyl) metal entity which is formed by reaction of the donated proton and the acceptor substituent of the first compound. Examples of such catalyst systems, normally regarded as polymerization catalysts, can be found in EP-A-277003 and the paper by Hlatky et al, J. Am. Chem. Soc., 1989, Vol. 111 p. 2728-2729.

The first component is typically a compound of zirconium or hafnium. The compound preferably has the formula $(Cp)_2MR_1R_2$where each group Cp, which may be the same or different, represents a cyclopentadienyl group of which at least one is (cyclo)alkyl and/or arylalkyl substituted, M represents a Group IVA metal atom, typically zirconium or hafnium, and $R_1$ and $R_2$ which may be the same or different, each represent a hydrogen atom or a substituted or unsubstituted hydrocarbyl group. Preferably, the groups Cp are the same and preferably have at least three substituents, more preferably, five substituents. The substituent(s) of the cyclopentadienyl are typically alkyl groups, in particular having up to 5 carbon atoms, more in particular they are methyl groups. Very good results can be achieved when both cyclopentadienyl groups are pentamethylcyclopentadienyl groups. $R_1$ and $R_2$ are preferably alkyl groups, typically of up to about 5 carbon atoms, such as methyl.

Such complexes are known and can be prepared for example by the routes described in "Chemistry of Organo-Zirconium and Hafnium Compounds", by Lappert et al., published by John Wiley & Sons.

The second component preferably contains, as the boron containing substantially non-coordinating anion, a carborane anion, suitably a carborane anion of formula $B_{11}CH_{12}^-$, while the cation is preferably a proton donating cation, preferably a quaternary ammonium cation such as a trialkylammonium cation, for example tri-n-butylammonium cation. Alternatively the cation may be a metal cation, such as a silver ion. Such carboranes are known and can be prepared for example by methods such as that of Shelly et al, J. Am. Chem. Soc. , 1985, Vol. 107, p. 5955 to 5959. Other bulky boron containing anions may be used such as a tetra(perfluorophenyl)boron anion.

The catalyst system may be formed by mixing together the two components, preferably in solution in a solvent such as toluene to form a liquid catalyst system. The two compounds are generally employed in substantially equimolar amounts. However the molar ratio of the first compound to the second compound may vary within the range of from 0.1 to 5.0. Such a quantity of the catalyst system is usually employed in the reaction mixture as to contain from about $10^{-1}$ to about $10^{-7}$ gram atom, in particular from about $10^{-3}$ to about $10^{-5}$ gram atom, of the Group IVA metal per mole of ethylene to be reacted.

The oligomerization is generally, although not necessarily, carried out in an inert liquid solvent which is suitably also the solvent for the catalyst components. The reaction can be carried out in batch or continuous operation. Reaction times of from about 1 minute to about 5 hours have been found to be suitable, dependent on the activity of the catalyst. After a suitable reaction time, a conventional catalyst deactivating agent such as methanol, or other alcohol, may be added if desired to the reaction mixture to terminate the reaction. The resulting mixed olefins preferably have a chain length of from about 5 to about 24 carbon atoms. The reaction is preferably carried out in the absence of air or moisture.

Product olefins are recovered suitably by distillation and further separated as desired by distillation techniques dependent on the intended end use of the olefins. If desired, unconverted starting material and oligomeric product having a molecular weight which is lower than the desired molecular weight may be recovered and recycled to be used as starting material in a subsequent oligomerization reaction.

The invention will now be further described with reference to the following examples which are for illustrative purposes and are not to be construed as limiting the invention.

EXAMPLES 1 and 2

The procedures were carried out with rigorous exclusion of oxygen and moisture.

Catalyst liquors were prepared by combining the following ingredients.

Catalyst liquor A, applied in Example 1:
- bis(cyclopentadienyl)zirconium dimethyl (0.251 g, 1.00 mmol).
- tri-n-butylammonium 1-carbadodecacarborate of formula $Bu_3NHB_{11}CH_{12}$ (0.329 g, 1.00 mmol, Bu=n-butyl),
- toluene (30 ml)

Catalyst liquor B, applied in Example 2:
- bis(pentamethylcyclopentadienyl)zirconium-dimethyl (0. 196 g, 0.50 mmol)
- $Bu_3NHB_{11}CH_{12}$ (0.164 g, 0.50 mmol)
- toluene (30 ml)

The catalyst liquors were added to an autoclave (500 ml volume) containing propene together with toluene (270 ml in Example 1, 70 ml in Example 2). The autoclave was then pressurized with ethene, using a predetermined quantity of ethene, and rapidly heated to the reaction temperature. Pressure was maintained by continuously recharging of consumed ethene. The product distribution was determined by gas-liquid chromatography (GLC) analyzing a sample taken from the content of the autoclave. At the end of the desired reaction time the reaction was terminated by releasing the pressure and treatment with methanol or exposure to air.

In order to assess the selectivity of the co-oligomerisation relative to ethene oligomerization a selectivity S is calculated which is defined by:

$$S = \frac{\text{yield of } C_5^= + C_7^= + C_9^= \text{ (moles)}}{\text{yield of } C_4^= + C_5^= + C_6^= + C_7^= + C_8^= + C_9^= \text{ (moles)}}.$$

Details of the reaction conditions and of the analytical results are given in Table 1.

TABLE 1

| Example | 1[1]) | | 2 |
|---|---|---|---|
| Catalyst liquor[2]) | A | | B |
| Propene charge (g) | 10 | | 23 |
| Ethene charge (g) | 19.3 | | 7 |
| Molar ratio $C_3^=/C_2^=$ | 0.35 | | 2.2 |
| Reaction temperature (°C.) | 125 | | 90 |
| Pressure (bar) | 30 | | 15 |
| Reaction time (min) | 30 | 2 | 15 |
| Olefin yields, GLC (g) | | | |
| $C_4$-$C_9$ olefins | 21.36 | 14.82 | 22.06 |
| $C_{10}^+$ olefins | 11.39 | — | 37.94 |
| Distribution $C_4$-$C_9$ olefins | | | |
| butene (g) | 7.02 | 0.82 | 1.78 |
| 1-butene (% w) | 47.8 | 86.6 | 83.7 |
| 2-butenes (% w) | 52.2 | 13.4 | 16.3 |
| pentenes (g) | 1.42 | 4.99 | 4.90 |
| 1-pentene (% w) | 50.1 | 84.0 | 73.9 |
| 2-pentenes (% w) | 35.9 | 15.5 | 25.5 |
| 2-methyl-1-butene (% w) | 14.0 | 0.6 | 0.6 |
| hexenes (g) | 6.49 | 1.01 | 2.75 |
| 1-hexene (% w) | 58.5 | 54.5 | 75.3 |
| 2-hexenes (% w) | 38.9 | 8.9 | 10.6 |
| 2-methyl-1-pentene (% w) | 2.6 | 36.6 | 14.2 |

TABLE 1-continued

| | | | |
|---|---|---|---|
| 4-methyl-1-pentene (% w) | 0.0 | 0.0 | 0.0 |
| heptenes (g) | 0.87 | 3.97 | 5.24 |
| 1-heptene (% w) | 59.4 | 83.4 | 76.2 |
| 2-heptenes (% w) | 29.8 | 15.4 | 22.9 |
| iso-heptene (% w) | 10.8 | 1.3 | 1.0 |
| octenes (g) | 4.85 | 0.97 | 2.72 |
| 1-octene (% w) | 66.1 | 50.5 | 75.4 |
| 2-octenes (% w) | 30.1 | 8.3 | 9.9 |
| iso-octenes (% w) | 3.8 | 41.2 | 14.7 |
| nonenes (g) | 0.71 | 3.06 | 4.83 |
| 1-nonene (% w) | 58.8 | 83.3 | 78.1 |
| 2-nonenes (% w) | 29.4 | 15.4 | 21.1 |
| iso-nonenes (% w) | 11.8 | 1.3 | 0.8 |
| Selectivity S (%) | 12 | 79 | 65 |

[1]) for comparison
[2]) A contained bis(cyclopentadienyl)zirconium dimethyl
B contained bis(pentamethylcyclopentadienyl)zirconium dimethyl

EXAMPLES 3, 4 AND 5

The procedures were carried out with rigorous exclusion of oxygen and moisture.

An autoclave (500 ml volume) was charged with toluene, ethene, propene and tri-n-butylamonium 1-carbadodecacarborate of formula $Bu_3NHB_{11}CH_{12}$. After heating the contents of the autoclave to the reaction temperature, a solution of one of the following metal compounds in about 10 ml toluene was introduced into the autoclave. In Example 3, bis(cyclopentadienyl)zirconium dimethyl was used as the metal compound, in Example 4, bis(pentamethylcyclopentadienyl)-zirconium dimethyl and in Example 5 bis(pentamethylcyclopentadienyl- hafnium dimethyl. After introduction of the metal compound, ethene was continuously supplied to the autoclave at a rate of about 0.3 g/min in Example 3 and at a rate of about 1 g/min in Example 5, while in Example 4 the pressure in the autoclave was maintained by continuously recharging of consumed ethene. The product distribution was determined by gas-liquid chromatography (GLC) analyzing a sample taken from the content of the autoclave. At the end of the desired reaction time the reaction was terminated by releasing the pressure and treatment with methanol or exposure to air. The selectivity is assessed by calculating the selectivity S as defined for Examples 1 and 2.

Details of the reaction conditions and of the analytical results are given in Table 2.

TABLE 2

| Example | 3[1]) | 4 | 5 |
|---|---|---|---|
| Metal compound (mmol) | 1.0[2]) | 0.05[3]) | 0.05[4]) |
| $Bu_3NHB_{11}CH_{12}$ (mmol) | 1.0 | 0.05 | 0.05 |
| Propene charge (g) | 300 | 100 | 100 |
| Ethene charge (g) | 3.0 | 0.5 | 0.5 |
| Molar ratio $C_3^=/C_2^=$ | 67 | 133 | 133 |
| Total volume of toluene (ml) | 300 | 100 | 100 |
| Reaction temperature (°C.) | 125 | 150 | 150 |
| Pressure (bar) | 30 | 50 | 50 |
| Reaction time (min) | 60 | 16 | 8 |
| Olefin yields, GLC (g) | | | |
| $C_4$-$C_9$ olefins | 3.37 | 5.83 | 16.29 |
| $C_{10}^+$ olefins | 0.17 | 0.35 | 2.42 |
| Distribution $C_4$-$C_9$ olefins | | | |
| butene (g) | 0.43 | 0.36 | 1.20 |
| 1-butene (% w) | 58.0 | 95.8 | 97.5 |
| 2-butenes (% w) | 42.0 | 4.2 | 2.5 |
| pentenes (g) | 1.70 | 3.01 | 8.95 |
| 1-pentene (% w) | 47.3 | 91.2 | 86.9 |
| 2-pentenes (% w) | 23.7 | 6.3 | 12.1 |
| 2-methyl-1-butene (% w) | 29.0 | 2.5 | 1.0 |
| hexenes (g) | 0.81 | 1.21 | 3.36 |
| 1-hexene (% w) | 11.5 | 8.5 | 2.4 |
| 2-hexenes (% w) | 8.5 | 0.8 | 0.6 |

TABLE 2-continued

| Example | 3[1]) | 4 | 5 |
|---|---|---|---|
| 2-methyl-1-pentene (% w) | 78.0 | 68.0 | 53.0 |
| 4-methyl-1-pentene (% w) | 2.0 | 22.7 | 44.0 |
| heptenes (g) | 0.31 | 0.96 | 2.09 |
| 1-heptene (% w) | 39.4 | 79.5 | 81.1 |
| 2-heptenes (% w) | 28.6 | 6.9 | 11.7 |
| iso-heptene (% w) | 32.0 | 13.7 | 7.1 |
| octenes (g) | 0.07 | 0.03 | 0.05 |
| 1-octene (% w) | 54.0 | 50.0 | 80 |
| 2-octenes (% w) | 36.0 | 6.7 | 10 |
| iso-octenes (% w) | 10 | 43.3 | 10 |
| nonenes (g) | 0.05 | 0.26 | 0.64 |
| 1-nonene (% w) | 48.0 | 76.8 | 48.0 |
| 2-nonenes (% w) | 32.0 | 6.6 | 6.9 |
| iso-nonenes (% w) | 20 | 16.6 | 45.1 |
| Selectivity S (%) | 61 | 72 | 71 |

[1])for comparison
[2])bis(cyclopentadienyl)zirconium dimethyl
[3])bis(pentamethylcyclopentadienyl)zirconium dimethyl
[4])bis(pentamethylcyclopentadienyl)hafnium dimethyl Examples 2, 4 and 5 are according to the invention. In these Examples the molar ratio of the additional alpha olefin to ethene is at least 1 and the cyclopentadienyl is alkyl substituted. Examples 1 and 3 are not according to the invention. They have been included as comparative examples. In Examples 1 and 3 the cyclopentadienyl group was unsubstituted. In Example 1 the molar ratio of the further alpha olefin to ethene is less than 1, whilst in Example 3 this ratio is at least 1.

By comparison of Examples 2-5 with Example 1, it can be seen that increase of the molar ratio of propene over ethene leads to a substantial increase of the selectivity S, which implies a substantial increase of the formation of co-oligomers of propene and ethene over the formation of oligomers of ethene. Comparison of Example 3 with Example 1 shows that the increase of the molar ratio of the olefins does not influence the relative quantities of the alpha olefins among the co-oligomerization products. Relatively high proportions of alpha olefins among the co-oligomerization products are achieved by using a bis(cyclopentadienyl) metal compound derived from an alkyl substituted cyclopentadienyl (cf. Example 2 vs. Example 1 and Examples 4 and 5 vs. Example 3). Examples 2, 4 and 5 show, in addition, that a relatively high proportion of the branched olefins which are formed in the co-oligomerization of propene and ethene are iso-alkenes having an even number of carbon atoms.

Comparative Example 1 of the present application is a reproduction of Example 6 of the European Patent Application 91200367.0, mentioned hereinbefore, supplemented with additional data. The amount of ethene initially present in the reaction mixtures of the Examples of EP-91200367.0 and the corresponding molar ratios of the further olefin to ethene are given in Table 3.

TABLE 3

| Example in EP-91200367.0 | Catalyst[1]) | Ethylene g | Molar ratio[2]) |
|---|---|---|---|
| 1 | C | 8.4 | 0.3 |
| 2 | C | 11.8 | 0.4 |
| 3 | D | 11.8 | 0.4 |
| 4 | C | 25 | 0.4 |
| 5 | C | 2.3 | 4.3 |
| 6[3]) | C | 19.3 | 0.3 |

TABLE 3-continued

| Example in EP-91200367.0 | Catalyst[1]) | Ethylene g | Molar ratio[2]) |
|---|---|---|---|
| 8 | E | 17.8 | 0.14 |

[1])C: contained bis(cyclopentadienyl)zirconium dimethyl
D: contained bis(pentamethylcyclopentadienyl)zirconium dimethyl
E: contained bis(pentamethylcyclopentadienyl)hafnium dimethyl
[2])of further alpha olefin to ethene
[3])Identical to Comparative Example 1 described hereinbefore The data of Table 3 shows that the reaction conditions of the Examples of EP-91200367.0 are outside the scope of the process of the invention.

What is claimed is:

1. A process for the preparation of olefins of the general formula $R-(CH_2-CH_2)_p-CH=CH_2$ in which formula R is a hydrocarbyl group and p is an integer of at least 1, comprising reacting ethene with at least one additional alpha olefin of the general formula $R-CH=CH_2$ under oligomerization conditions in the presence of a catalyst system comprising a first component which is a bis(cyclopentadienyl) Group IVA metal compound containing a substituent which is attached to the metal and which is capable of reacting with a cation, and a second component which is a compound having a bulky anion containing a plurality of boron atoms and which is substantially non-coordinating under the reaction conditions and a cation, and thereafter recovering an oligomeric product comprising linear olefins of the general formula $R1-(CH_2-CH_2)_p-CH=CH_2$, wherein the additional alpha olefin(s) and ethene are present in a molar ratio of at least 1 and wherein at least one of the cyclopentadienyl groups of the metal compound is substituted with a group selected from the group consisting of (cyclo)alkyl, arylalkyl, and mixtures thereof.

2. The process according to claim 1, wherein the additional alpha olefin is a linear olefin having an odd number of carbon atoms.

3. The process according to claim 2, wherein the additional alpha olefin is propene.

4. The process according to claim 2, wherein the oligomerization products, which have odd numbers of carbon atoms in their chains, are recovered.

5. The process according to claim 1, wherein the ratio of the additional alpha olefin(s) to ethene is within the range of from 50 to 500 moles per mole ethene.

6. The process according to claim 1, wherein the oligomerization is carried out at a temperature within the range of from about 50° C. to about 150° C.

7. The process according to claim 1, wherein the oligomerization is carried out at a pressure within the range of from about 5 bar to about 60 bar.

8. The process according to claim 1, wherein the molar ratio of the first compound to the second compound is within the range of from about 0.1 to about 5.0.

9. The process according to claim 1, wherein a quantity of the catalyst system is used in the reaction mixture such that said mixture contains from about $10^{-3}$ to about $10^{-5}$ gram atom of the Group IVA metal per mole of ethylene to be reacted.

10. The process according to claim 1, wherein the first component of the catalyst system is a compound of formula $(Cp)_2MR_1R_2$ where each group Cp, which is the same or different, represents a cyclopentadienyl group of which at least one is (cyclo)alkyl and/or arylalkyl substituted, M represents a group IVA metal atom, and $R_1$ and $R_2$, which may be the same or different, each represent a hydrogen atom or a substituted or unsubstituted hydrocarbyl group.

11. The process according to claim 10, wherein M is selected from the group consisting of zirconium and hafnium.

12. The process according to claim 10, wherein each group Cp represents a pentamethylcyclopentadienyl group and $R_1$ and $R_2$ are each alkyl groups.

13. The process according to claim 1, wherein the second component of the catalyst system comprises a carborane anion as the substantially non-coordinating anion.

14. The process according to claim 13, wherein the second component of the catalyst system comprises a proton-donating cation.

15. The process according to claim 13, wherein the second component of the catalyst system is a trialkylammonium carborane wherein the carborane anion being represented by the formula $B_{11}CH_{12}^-$.

* * * * *